United States Patent [19]
Rovnyak

[11] 4,128,648
[45] Dec. 5, 1978

[54] SUBSTITUTED PYRANO[4,3-d]-THIAZOLO[3,2-a]PYRIMIDINES

[75] Inventor: George C. Rovnyak, Hopewell, N.J.
[73] Assignee: E. R. Squibb & Sons, Inc., Princeton, N.J.
[21] Appl. No.: 889,714
[22] Filed: Mar. 24, 1978
[51] Int. Cl.² .................. A61K 31/18; C07D 405/14
[52] U.S. Cl. .................. 424/251; 424/246; 542/449; 544/34; 544/252
[58] Field of Search ............ 542/449; 424/251, 246; 544/34, 250, 251, 252

[56] References Cited
U.S. PATENT DOCUMENTS
3,636,041  1/1972  Schmidt et al. ............ 544/250 X
3,657,245  4/1972  Bormann et al. ............ 544/250

FOREIGN PATENT DOCUMENTS
4225916  5/1965  Japan ............................ 544/34
1242863  8/1971  United Kingdom .......... 544/250

OTHER PUBLICATIONS
Khodzhibaev et al., "Reaction of CO with 4-Me-5-carbethoxy-2-aminothiazole," in Chem. Abs. 85:21277r, 1976, vol. 85, p. 21285.

Primary Examiner—Allen B. Curtis
Attorney, Agent, or Firm—Lawrence S. Levinson; Merle J. Smith; Burton Rodney

[57] ABSTRACT 2,3,8,9-Tetrahydro-5H,6H-pyrano[4,3-d]thiazolo[3,2-a]pyrimidines of the structure

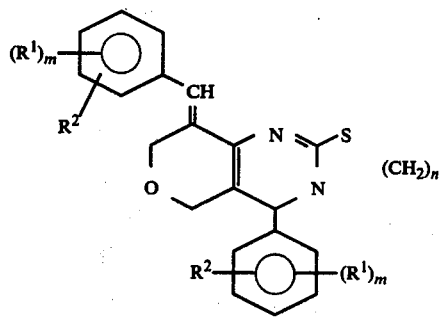

are provided wherein $R^1$ and $R^2$ may be the same or different and are hydrogen, lower alkyl, halogen, cyano, carbethoxy, carboxyl, trifluoromethyl or lower alkoxy, and $n$ is 2 or 3, and $m$ is 0 to 2. These compounds are useful in the treatment of auto-immune disorders, such as rheumatoid arthritis.

11 Claims, No Drawings

SUBSTITUTED PYRANO[4,3-d]-THIAZOLO[3,2-a]PYRIMIDINES

FIELD OF THE INVENTION

The present invention relates to substituted pyrano[4,3-d]thiazolo[3,2-a]pyrimidines and more particularly to 2,3,8,9-tetrahydro-5H,6H-pyrano[4,3-d]thiazolo[3,2-a]pyrimidines, and their use in the treatment of auto-immuno disorders, such as rheumatoid arthritis.

DESCRIPTION OF THE INVENTION

The 2,3,8,9-tetrahydro-5H,6H-pyrano[4,3-d]thiazolo[3,2-a]pyrimidines of the invention have the formula

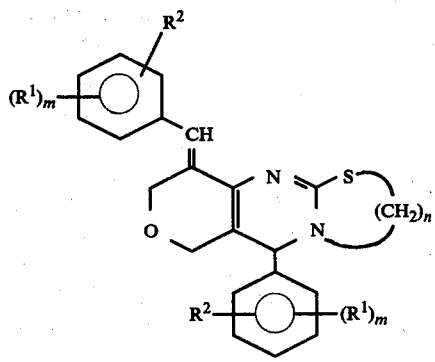

wherein $R^1$ and $R^2$ may be the same or different and are hydrogen, lower alkyl, halogen, cyano, carbethoxy, carboxyl, trifluoromethyl or lower alkoxy, $n$ is 2 or 3 and $m$ is 0 to 2.

Preferred are those compounds of formula I wherein $n$ is 2, $m$ is 0 to 2 and $R^1$ is hydrogen or lower alkyl, di-lower alkyl, lower alkoxy, di-lower alkoxy or tri-lower alkoxy, and $R^2$ is hydrogen or lower alkoxy.

The terms "alkyl" and "alkoxy" as used herein (individually or as part of a larger group) refer to groups having 1 to 8 carbon atoms; alkyl and alkoxy groups having 1 to 3 carbon atoms are preferred.

The term "halogen" as used herein refers to fluorine, chlorine, bromine and iodine; fluorine and chlorine are preferred.

Compounds of formula I may be prepared by reaction of an unsaturated ketone of formula II with an amino compound of formula III employing a mole ratio of II:III of within the range of from about 1:1 to about 1:3, and preferably from about 1:1 to about 1:2. The reaction will be carried out in a suitable mixed organic solvent system, for example a lower alkanol, such as n-butanol, and dimethyl sulfoxide (approximate 10:4 ratio) preferably at reflux temperature of periods ranging from 0.5 to 24 hours, and preferably from 2 to 4 hours.

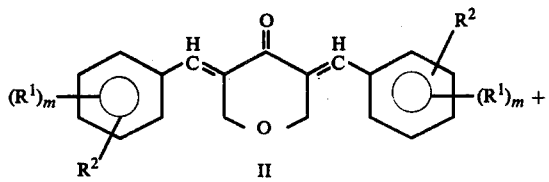

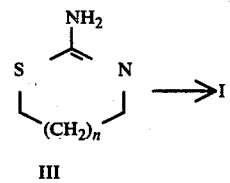

Alternatively, compounds of formula I may be formed by treatment of an intermediate aminol of formula IV with 1 to 2 equivalents of a Lewis acid, preferably TiCl₄, in an aprotic solvent, such as toluene, while heating at reflux temperature for from 0.5 to 2 hours.

The intermediate aminol IV may also be cyclo-dehydrated to I by heating in a mixture of n-butanol and DMSO (preferably in a ratio of 10:4) for from 0.5 to 24 hours, preferably for from 2 to 4 hours.

Compounds of formula IV are prepared by reacting, as above, an amino compound of formula III with an unsaturated ketone of formula II, but under milder conditions such as performing the reaction in a solvent in which the formed aminol IV is sparingly soluble. The preferred solvent is acetone or methyl ethyl ketone but a chlorinated solvent such as chloroform may also be used, and the preferred temperature for this reaction is ambient although heating at reflux temperature is sometimes necessary.

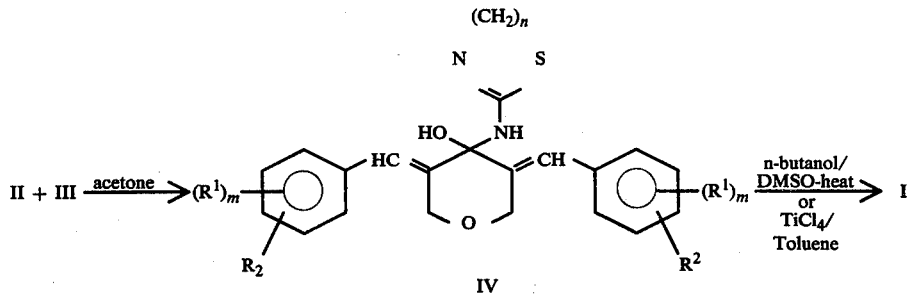

Unsaturated ketones of formula II are prepared as described in J.A.C.S., 79, 156 (1957). Amines of formula III are obtained either commercially ($n=2$) or are prepared ($n=3$) as described in J.O.C., 31, 2349 (1966).

The compounds of formula I form acid-addition salts with inorganic and organic acids. These acid-addition salts frequently provide useful means for isolating the products from reaction mixtures by forming the salt in a medium in which it is insoluble. The free base may then be obtained by neutralization, e.g., with a base such as sodium hydroxide. Any other salt may then be formed from the free base and the appropriate inorganic or organic acid. Illustrative are the hydrohalides, especially the hydrochloride and hydrobromide, sulfate, nitrate, phosphate, borate, acetate, tartrate, maleate, citrate, succinate, oxalate, benzoate, ascorbate, salicylate, methanesulfonate, benzenesulfonate, toluenesulfonate and the like. Preferred salts are the hydrochlorides and maleates.

The compounds of the invention have antiinflammatory activity as measured by the mouse active arthus (MAA) test and are useful as antiinflammatory agents and are effective in the prevention and inhibition of granuloma tissue formation in warm blooded animals, and may be used, for example, in a manner similar to phenylbutazone or indomethacin. They may be used to decrease joint swelling, tenderness, pain and stiffness in mammalian species, such as dogs and monkeys, e.g., in conditions such as rheumatoid arthritis. Compounds of formula I or a physiologically acceptable acid-addition salt thereof may be compounded for such use according to accepted pharmaceutical practice in oral dosage forms such as tablets, capsules, elixirs or powders or in injectable form for administration of about 100 mg to 2 gm per day, preferably 100 mg to 1 gm per day in two to four divided doses.

The following examples further illustrate and represent preferred embodiments of the invention. All temperatures are expressed in degrees Centigrade.

EXAMPLE 1

2,3,8,9-Tetrahydro-5-phenyl-9-(phenylmethylene)-5H,6H-pyrano[4,3-d]thiazolo[3,2-a]pyrimidine

A.

4-[(4,5-Dihydro-2-thiazolyl)amino]tetrahydro-3,5-bis(-phenylmethylene)-2H-pyran-4-ol A solution of 2-amino-2-thiazoline (2.2 g, 22 mmole) in 100 ml of acetone is added to a suspension of tetrahydro-3,5-bis(phenylmethylene)-4H-pyran-4-one (5.0 g, 18 mmole) in 50 ml of acetone and heated at reflux temperature for 5 hours and then kept at room temperature overnight. Chloroform (75 ml) is added to the stirred mixture and, after 10 minutes, the product is collected and washed with acetone to give 3.1 g of crude product. When the filtrate, concentrated and resuspended in acetone, is stirred with additional 2-amino-2-thiazoline (2.2 g) at room temperature overnight, another 2.5 g is isolated for a combined yield of 5.6 g (82%).

B.

2,3,8,9-Tetrahydro-5-phenyl-9-(phenylmethylene)-5H,6H-pyrano[4,3-d]thiazolo[3,2-a]pyrimidine To a stirred suspension of 4-[(4,5-dihydro-2-thiazolyl)amino]tetrahydro-3,5-bis(phenylmethylene)-2H-pyran-4-ol (2.5 g, 6.6 mmole) in toluene (100 ml) is added slowly a solution of titanium tetrachloride (0.63 g, 3.3 mmole) in toluene (6.1 ml). The yellow mixture is heated at reflux temperature for 45 minutes.

Upon cooling, the solid precipitate is pulverized and filtered. The solids are then dissolved in CHCl₃ and washed with dilute aqueous NaOH solution and H₂O. The organic phase is dried (MgSO₄) and concentrated on a steam bath. Methanol is added frequently to maintain the volume at 150 ml. When crystals start to appear in the warm mixture, it is cooled to room temperature, giving 1.4 g (59%) of the product, m.p. 225°–227° (d).

EXAMPLE 2

2,3,8,9-Tetrahydro-5-(4-methoxyphenyl)-9-[(4-methoxyphenyl)-methylene]-5H,6H-pyrano[4,3-d]thiazole[3,2-a]pyrimidine A mixture of tetrahydro-3,5-bis(phenylmethylene)-4H-pyran-4-one (4.8 g, 14 mmole) and 2-amino-2-thiazoline (2.1 g, 21 mmole) in 200 ml of $CHCl_3$ containing 3A molecular sieves is heated at reflux temperature for 24 hours. Additional 2-amino-2-thiazoline (1.0 g, 10 mmole) is added and heating is continued for another 24 hours, when tlc indicates loss of starting ketone ($R_f = 0.90$) and appearance of a major new spot ($R_f = 0.75$) in 5% MeOH/CHCl₃ (silica gel). The mixture is filtered and concentrated in vacuo to a small volume and heated on a steam bath as MeOH is added. Upon cooling, there is obtained 3.0 g, m.p. 155° d. This is recrystallized (from CHCl₃/MeOH) along with 1.4 g from a previous run to give 3.5 g (33%) of product, m.p. 167°–170° (soften 164°).

EXAMPLE 3

2,3,8,9-Tetrahydro-5-(3,4,5-trimethoxyphenyl)-9-[(3,4,5-trimethoxyphenyl)methylene]-5H,6H-pyrano[4,3-d]thiazolo[3,2-a]pyrimidine

A.

Tetrahydro-3,5-bis[(3,4,5-trimethoxyphenyl)methylene]-4H-pyran-4-one

A solution of 6.0 g (0.06 mole) of tetrahydro-4H-pyran-4-one and 25 g (0.127 mole) of 3,4,5-trimethoxybenzaldehyde in 75 ml of EtOH and 10 ml of concentrated HCl is stirred and heated at reflux for 3 hours. The product gradually precipitates from the cooled solution. The yield of yellow crystals is 12.0 g (44%), m.p. 187°–189°.

B.

2,3,8,9-Tetrahydro-5-(3,4,5-trimethoxyphenyl)-9-[(3,4,5-trimethoxyphenyl)methylene]-5H,6H-pyrano[4,3-d]thiazolo[3,2-a]pyrimidine A stirred solution of tetrahydro-3,5-bis[(3,4,5-trimethoxyphenyl)methylene]-4H-pyran-4-one (3.0 g, 6.5 mmole) and 2-amino-2-thiazoline (0.8 g, 7.8 mmole) in 75 ml of CHCl₃ is heated at reflux for 44 hours. After cooling, the solution is filtered to remove a small amount of insoluble material. The solvent is evaporated to give an oily residue which solidifies when treated with a small amount of EtOH. The yield is 2.2 g, m.p. 166°–168°. Crystallization from 10 ml of MeCN gives 1.5 g (42%) of light yellow solid, m.p. 153°–155°. The m.p. of a sample of this material does not change when recrystallized from MeCN.

EXAMPLE 4

2,3,8,9-Tetrahydro-5-(4-methoxy-2,3-dimethylphenyl)-9-[(4-methoxy-2,3-dimethylphenyl)methylene]-5H,6H-pyrano[4,3-d]thiazolo[3,2-a]pyrimidine

A.

Tetrahydro-3,5-bis[(4-methoxy-2,3-dimethylphenyl)methylene]-4H-pyran-4-one

A solution of 6.0 g (0.06 mole) of tetrahydro-4H-pyran-4-one, 21.6 g (0.13 mole) of 2,3-dimethyl-p-anisaldehyde in 75 ml of EtOH and 10 ml of concentrated HCl is stirred and heated at reflux for 3 hours. The product gradually precipitates during this period. After cooling, this material is filtered and treated with ether to give 9.1 g (39%) of yellow crystals, m.p. 225°–227°.

B.
2,3,8,9-Tetrahydro-5-(4-methoxy-2,3-dimethylphenyl)-9-[(4-methoxy-2,3-dimethylphenyl)-methylene]-5H,6H-pyrano[4,3-d]thiazolo[3,2-a]pyrimidine A stirred solution of tetrahydro-3,5-bis[(4-methoxy-2,3-dimethylphenyl)methylene]-4H-pyran-4-one (3.0 g, 7.6 mmole) and 2-amino-2-thiazoline (1.0 g, 9.7 mmole) in 75 ml of CHCl₃ is heated at reflux temperature for 72 hours. After cooling, the solution is filtered to remove a small amount of insoluble material. The solvent is evaporated to give an oily residue. Trituration with warm EtOH yields 2.7 g of a yellow solid, m.p. 226°–228° d.

orated to give an oily residue. A solution of this material in 25 ml of EtOH yields 1.7 g of light yellow solid, m.p. 195°–197°. Crystallization from 20 ml of 10% DMF/MeOH gives 1.3 g (35%) of cream colored solid, m.p. 196°–198°.

EXAMPLES 6 TO 14

Following the procedure of Example 2, except substituting for tetrahydro-3,5-bis(phenylmethylene)-4H-pyran-4-one, the compound shown in Column I of Table I set out below, and substituting for 2-amino-2-thiazoline, the compound shown in Column II, the product shown in Column III is obtained.

TABLE I

| Ex. No. | Column I | | Column II | Column III | | |
|---|---|---|---|---|---|---|
| | $(R^1)_m$(position) | $R^2$(position) | n | $(R^1)_m$(position) | $R^2$(position) | n |
| 6. | (CH₃)₂ (3,4) | CH₃ (5) | 2 | as in Column I | | as in Column II |
| 7. | (Cl)₂ (3,5) | H | 2 | | | |
| 8. | CN (4) | H | 2 | | | |
| 9. | (—COOC₂H₅)₂ (3,5) | H | 2 | | | |
| 10. | (COOH) (4) | H | 3 | | | |
| 11. | (CF₃) (4) | H | 3 | | | |
| 12. | (CN) (3) | H | 3 | | | |
| 13. | (Br) (3,5) | Br (4) | 3 | | | |
| 14. | (CF₃) (3) | H | 2 | | | |

Crystallization from 15 ml of DMF gives 2.3 g (63%) of cream colored product, m.p. 235°–237°.

EXAMPLE 5

2,3,8,9-Tetrahydro-5-(4-methoxy-2,5-dimethylphenyl)-9-[(4-methoxy-2,5-dimethylphenyl)methylene]-5H,6H-pyrano[4,3-d]thiazolo[3,2-a]pyrimidine

A.
Tetrahydro-3,5-bis[(4-methoxy-2,5-dimethylphenyl)methylene]-4H-pyran-4-one A solution of 7.0 g (0.07 mole) of tetrahydro-4H-pyran-4-one and 25.2 g (0.15 mole) of 2,5-dimethyl-p-anisaldehyde in 75 ml of EtOH and 10 ml of concentrated HCl is stirred and heated at reflux for 3 hours. The resulting mixture is kept at room temperature for 24 hours, yielding 10.7 g (39%) of yellow solid, m.p. 182°–184°.

B.
2,3,8,9-Tetrahydro-5-(4-methoxy-2,5-dimethylphenyl)-9-[(4-methoxy-2,5-dimethylphenyl)methylene]-5H,6H-pyrano[4,3-d]thiazolo[3,2-a]pyrimidine A stirred solution of tetrahydro-3,5-bis[(4-methoxy-2,5-dimethylphenyl)methylene]-4H-pyran-4-one (3.0 g, 7.6 mmole) and 2-amino-2-thiazoline (1.0 g, 9.7 mmole) in 75 ml of CHCl₃ is heated at reflux temperature for 72 hours. After cooling, the solution is filtered to remove a small amount of insoluble material. The solvent is evap-

What is claimed is:

1. A compound of the structure

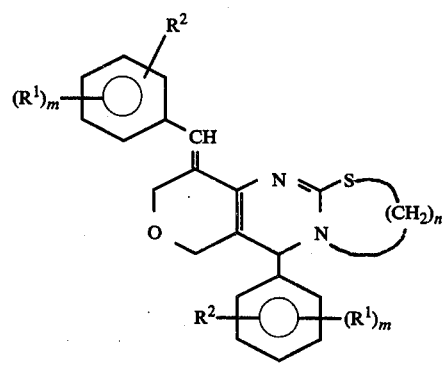

wherein $R^1$ and $R^2$ may be the same or different and are selected from the group consisting of hydrogen, lower alkyl, halogen, carbethoxy, cyano, carboxyl, trifluoromethyl, and lower alkoxy, m is 0 to 2 and n is 2 or 3, and pharmaceutically acceptable salts thereof.

2. The compound of claim 1 wherein n is 2.

3. The compound of claim 1 wherein $(R^1)_m$ is hydrogen lower alkyl, dilower alkyl, lower alkoxy, dilower alkoxy or trilower alkoxy.

4. The compound of claim 1 wherein n is 2, m is 0 or 2, and R is hydrogen, methyl or methoxy.

5. The compound of claim 1 having the name 2,3,8,9-tetrahydro-5-(4-methoxyphenyl)-9-[(4-methoxyphenyl)methylene]-5H,6H-pyrano[4,3-d]thiazolo[3,2-a]pyrimidine.

6. The compound of claim 1 having the name 2,3,8,9-tetrahydro-5-phenyl-9-(phenylmethylene)-5H,6H-pyrano[4,3-d]thiazolo[3,2-a]pyrimidine.

7. The compound of claim 1 having the name 2,3,8,9-tetrahydro-5-(3,4,5-trimethoxyphenyl)-9[(3,4,5-trimethoxyphenyl)methylene]-5H,6H-pyrano[4,3-d]thiazolo[3,2-a]pyrimidine.

8. The compound of claim 1 having the name 2,3,8,9-tetrahydro-5-(4-methoxy-2,3-dimethylphenyl)-9-[(4-methoxy-2,3-dimethylphenyl)methylene]-5H,6H-pyrano[4,3-d]thiazolo[3,2-a]pyrimidine.

9. The compound of claim 1 having the name 2,3,8,9-tetrahydro-5-(4-methoxy-2,5-dimethylphenyl)-9-[(4-methoxy-2,5-dimethylphenyl)methylene]-5H,6H-pyrano[4,3-d]thiazolo[3,2-a]pyrimidine.

10. A pharmaceutical composition for use in treating inflammatory conditions comprising an effective amount of an anti-inflammatory compound as defined in claim 1 and a pharmaceutically acceptable carrier therefor.

11. A method for treating an inflammatory condition in a mammalian host, which comprises administering to said host a therapeutically effective amount of a compound as defined in claim 1.

* * * * *

UNITED STATES PATENT AND TRADEMARK OFFICE
CERTIFICATE OF CORRECTION

PATENT NO. : 4,128,648
DATED : December 5, 1978
INVENTOR(S) : George C. Rovnyak

It is certified that error appears in the above-identified patent and that said Letters Patent are hereby corrected as shown below:

Table I, Column III, the structure should read as follows:

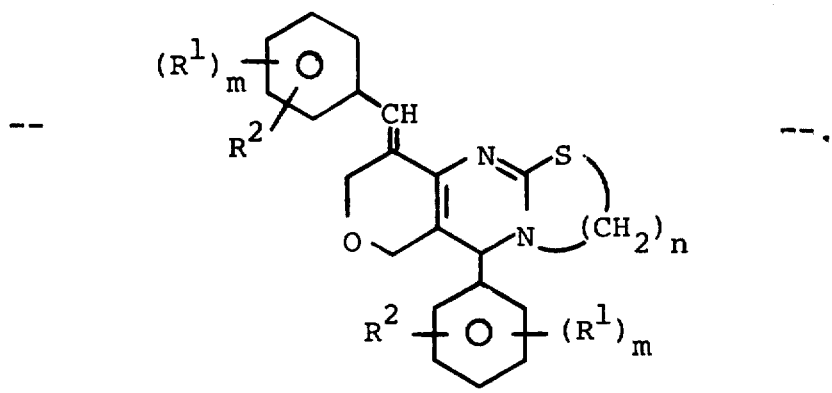

Signed and Sealed this

Twenty-seventh Day of March 1979

[SEAL]

Attest:

RUTH C. MASON
Attesting Officer

DONALD W. BANNER
Commissioner of Patents and Trademarks